United States Patent
Swanson

(10) Patent No.: US 8,758,335 B2
(45) Date of Patent: *Jun. 24, 2014

(54) INTERNAL INDIFFERENT ELECTRODE DEVICE FOR USE WITH LESION CREATION APPARATUS AND METHOD OF FORMING LESIONS USING THE SAME

(75) Inventor: David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2034 days.

This patent is subject to a terminal disclaimer.

(21) Appl. No.: 11/864,567

(22) Filed: Sep. 28, 2007

(65) Prior Publication Data
US 2008/0021446 A1    Jan. 24, 2008

Related U.S. Application Data

(63) Continuation of application No. 10/980,845, filed on Nov. 3, 2004, now Pat. No. 7,288,090, which is a continuation of application No. 09/801,416, filed on Mar. 7, 2001, now Pat. No. 6,827,714.

(51) Int. Cl.
*A61B 18/04* (2006.01)

(52) U.S. Cl.
USPC .............................................. 606/35; 606/41

(58) Field of Classification Search
USPC ................. 606/31, 39, 41, 49–51, 35
See application file for complete search history.

(56) References Cited

U.S. PATENT DOCUMENTS

| | | |
|---|---|---|
| 4,011,872 A | 3/1977 | Komiya |
| 4,493,320 A | 1/1985 | Treat |
| 4,532,924 A | 8/1985 | Auth et al. |
| 4,651,734 A | 3/1987 | Doss et al. |
| 4,776,334 A * | 10/1988 | Prionas ........................... 606/42 |
| 5,249,121 A * | 9/1993 | Baum et al. ........................ 606/1 |
| 5,562,720 A | 10/1996 | Stern et al. |
| 5,582,609 A | 12/1996 | Swanson et al. |
| 5,630,426 A | 5/1997 | Eggers et al. |
| 5,685,839 A * | 11/1997 | Edwards et al. ................ 604/22 |
| 5,868,742 A | 2/1999 | Manes et al. |
| 5,871,523 A | 2/1999 | Fleischman et al. |
| 5,876,400 A * | 3/1999 | Songer ............................ 606/45 |
| 5,895,386 A | 4/1999 | Odell et al. |
| 5,935,079 A | 8/1999 | Swanson et al. |
| 5,947,964 A | 9/1999 | Eggers et al. |
| 5,961,207 A * | 10/1999 | Petkovic ....................... 362/376 |
| 5,999,835 A | 12/1999 | Osypka |

(Continued)

FOREIGN PATENT DOCUMENTS

| WO | WO 98/19611 A1 | 5/1998 |
|---|---|---|
| WO | WO 99/18869 A1 | 4/1999 |
| WO | WO 01/12090 A1 | 2/2001 |

OTHER PUBLICATIONS

Office Action dated May 8, 2008 in corresponding JP App. Ser. No. 2002-569234 including English language translation.

*Primary Examiner* — Patricia Bianco
*Assistant Examiner* — Camtu Nguyen
(74) *Attorney, Agent, or Firm* — Seager, Tufte & Wickhem, LLC

(57) ABSTRACT

An internal indifferent electrode device including a flexible shaft, an energy transmission device adapted to be inserted into the body supported on the shaft, and a connector adapted to mate with the power return connector of a power supply apparatus.

5 Claims, 6 Drawing Sheets

(56) References Cited

U.S. PATENT DOCUMENTS

| | | |
|---|---|---|
| 6,071,281 A | 6/2000 | Burnside et al. |
| 6,142,994 A | 11/2000 | Swanson et al. |
| 6,171,306 B1 | 1/2001 | Swanson et al. |
| 6,287,304 B1 * | 9/2001 | Eggers et al. .................. 606/37 |
| 6,290,699 B1 * | 9/2001 | Hall et al. ...................... 606/41 |
| 6,527,767 B2 | 3/2003 | Wang et al. |
| 6,546,935 B2 | 4/2003 | Hooven |
| 6,780,048 B2 * | 8/2004 | Chen et al. .................... 439/502 |
| 6,827,714 B2 | 12/2004 | Swanson |
| 7,288,090 B2 | 10/2007 | Swanson |
| 2005/0085805 A1 | 4/2005 | Swanson |

* cited by examiner

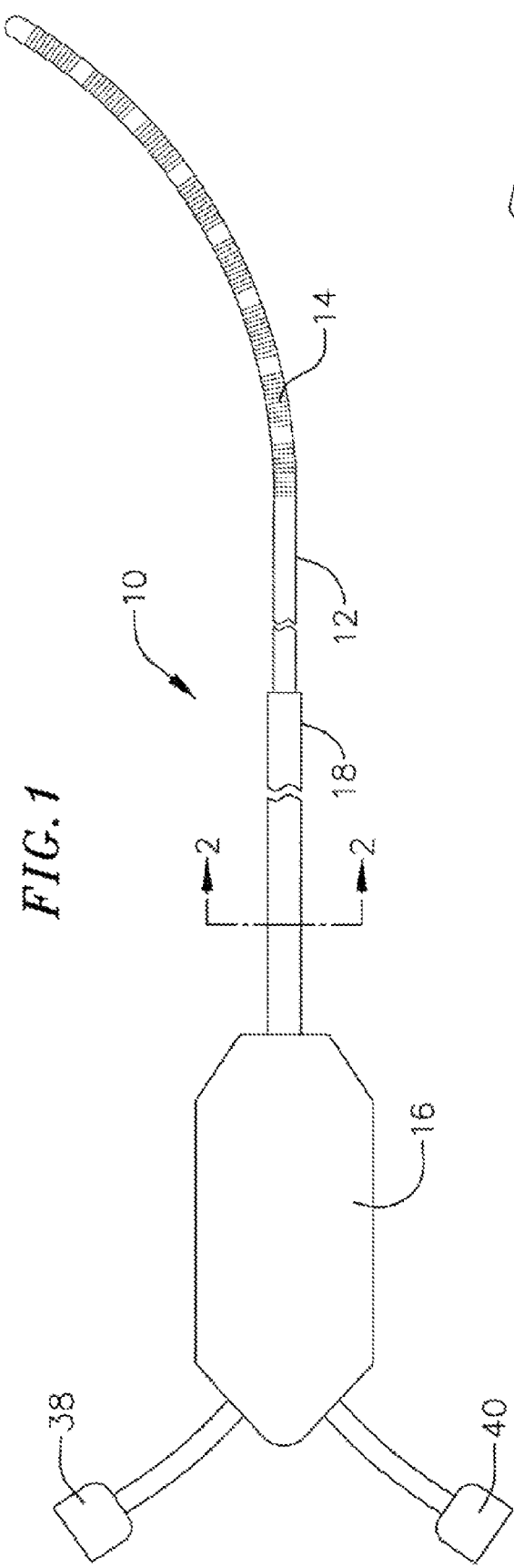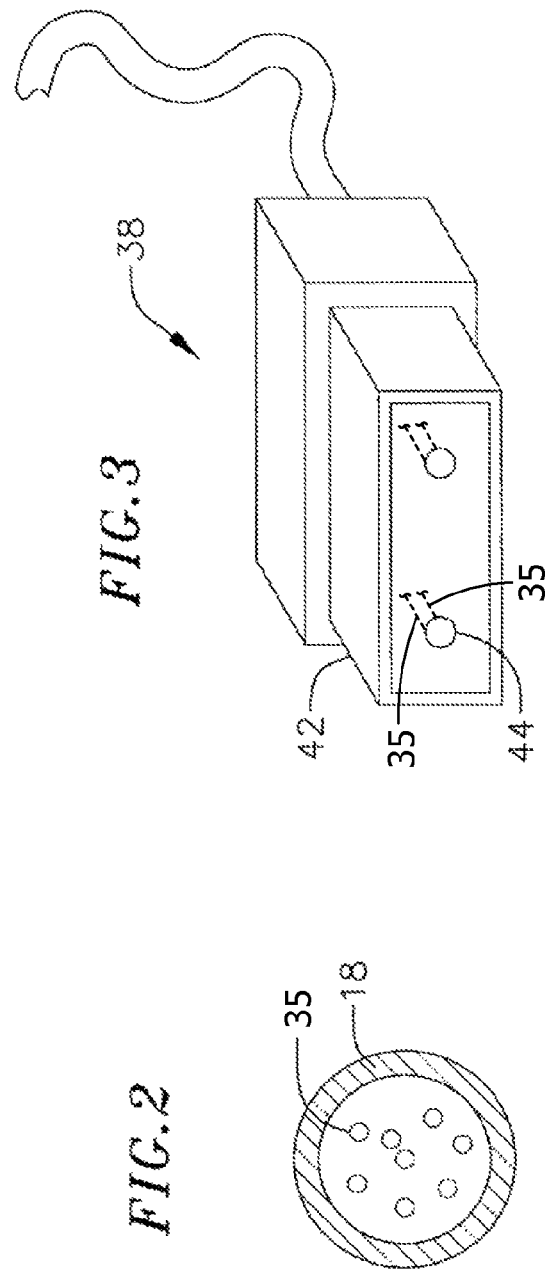

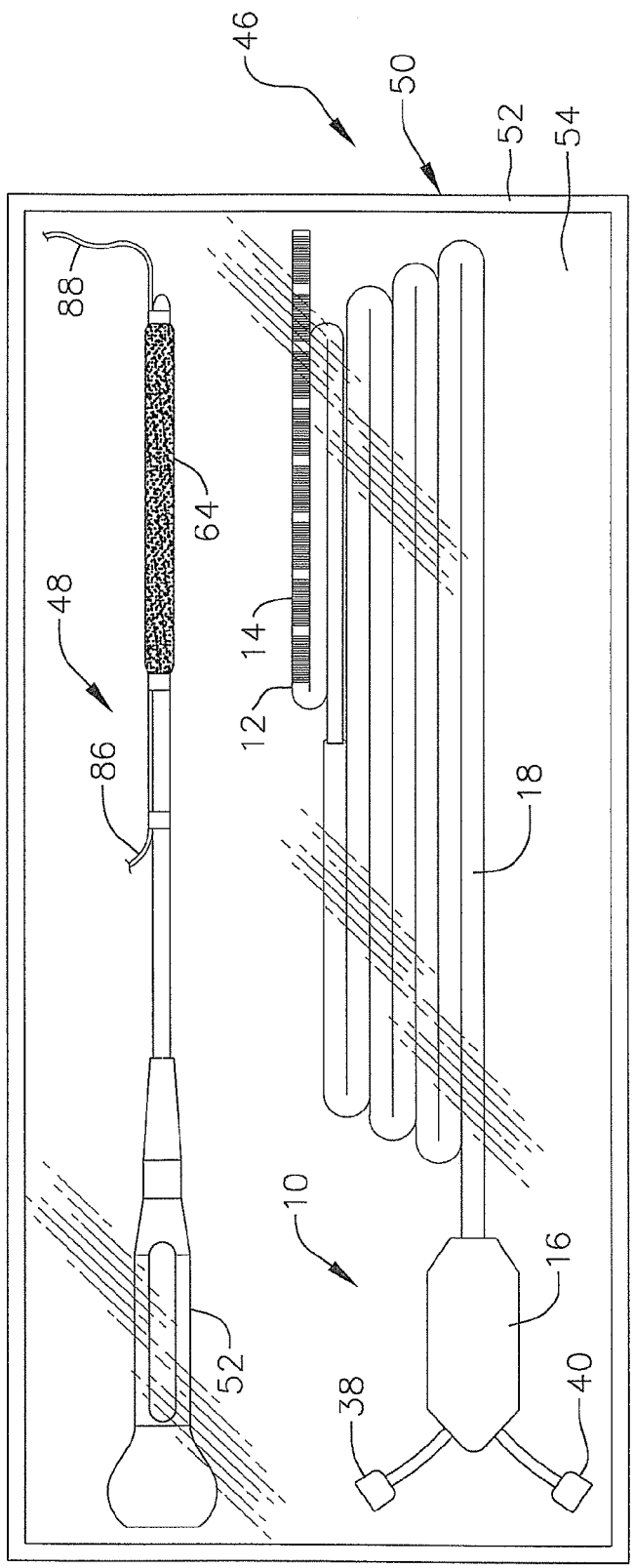

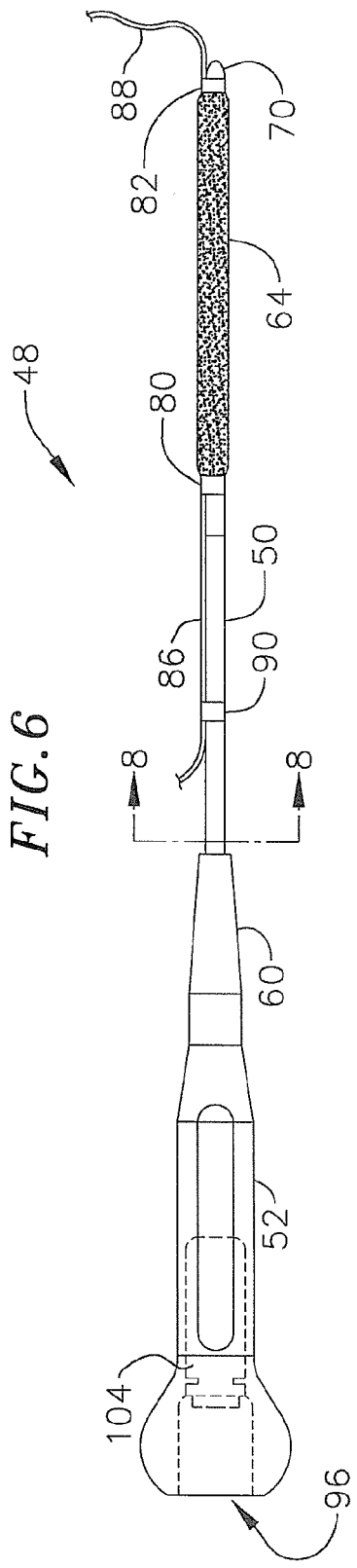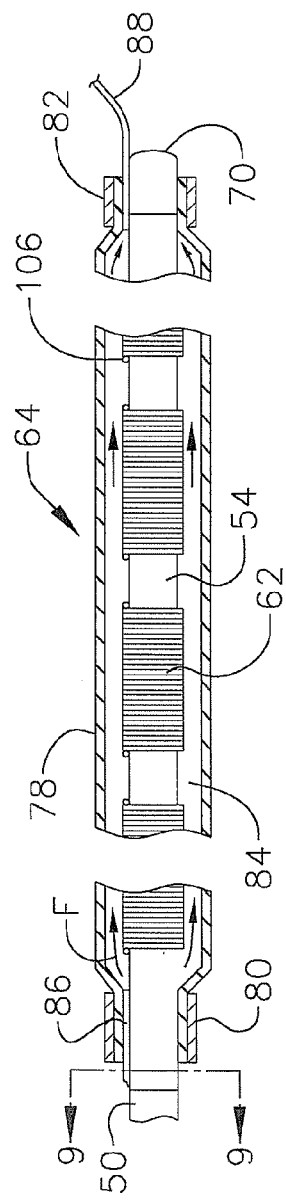

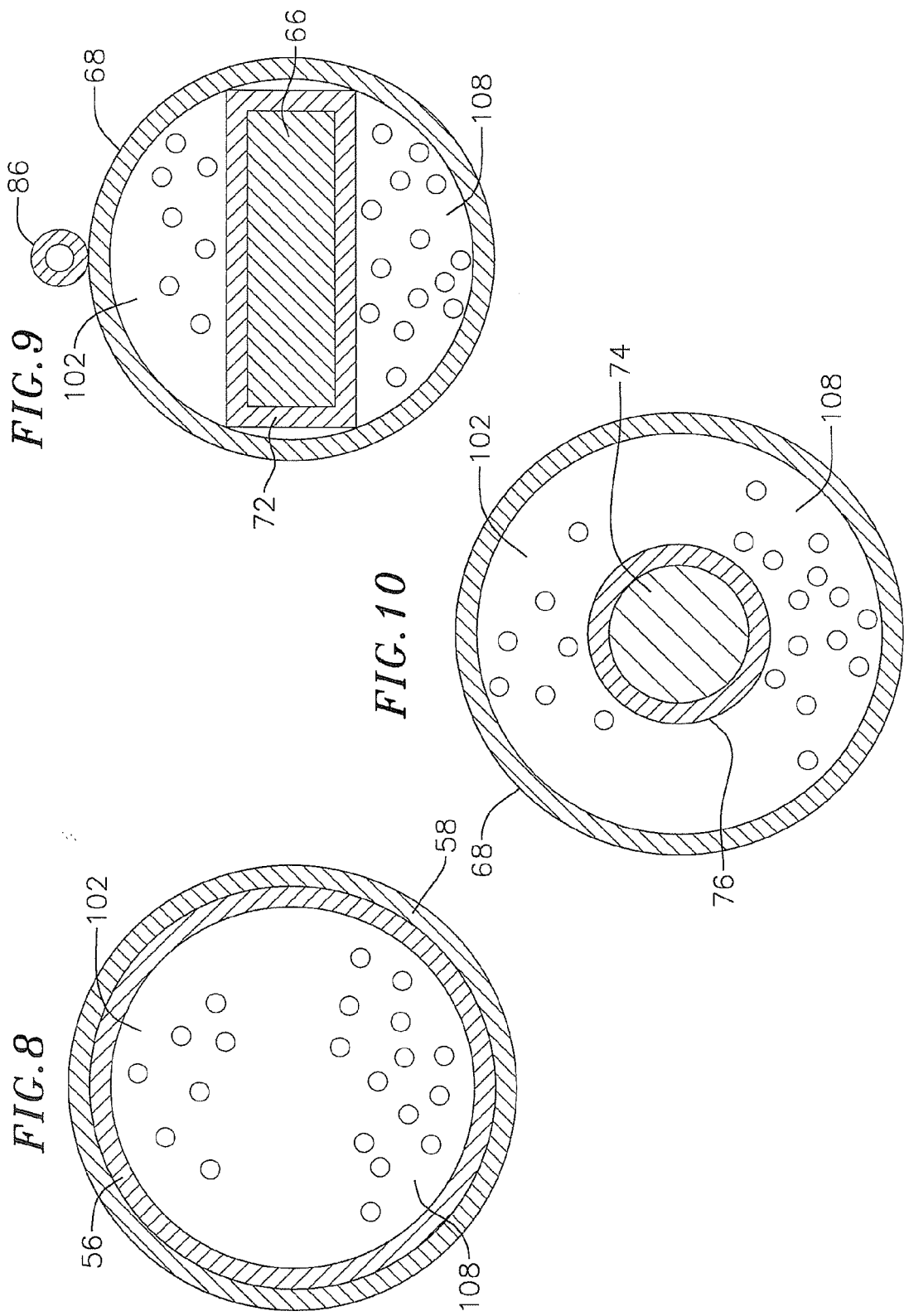

INTERNAL INDIFFERENT ELECTRODE DEVICE FOR USE WITH LESION CREATION APPARATUS AND METHOD OF FORMING LESIONS USING THE SAME

This application is a continuation of application Ser. No. 10/980,845, filed Nov. 3, 2004, now U.S. Pat. No. 7,288,090, which is a continuation of application Ser. No. 09/801,416, filed Mar. 7, 2001, now U.S. Pat. No. 6,827,714.

BACKGROUND OF THE INVENTIONS

1. Field of the Inventions

The present inventions relate generally to electrophysiological devices and, more particularly, to the indifferent electrodes that are used in conjunction with electrophysiological devices.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

Although pharmacological treatment is available for atrial fibrillation and flutter, the treatment is far from perfect. For example, certain antiarrhythmic drugs, like quinidine, amiodarone, and procainamide, can reduce both the incidence and the duration of atrial fibrillation episodes. Yet, these drugs often fail to maintain sinus rhythm in the patient. Cardioactive drugs, like digitalis, Beta blockers, and calcium channel blockers, can also be given to control the ventricular response. However, many people are intolerant to such drugs. Anticoagulant therapy also combats thromboembolic complications, but does not eliminate them. Unfortunately, pharmacological remedies often do not remedy the subjective symptoms associated with an irregular heartbeat. They also do not restore cardiac hemodynamics to normal and remove the risk of thromboembolism.

Many believe that the only way to really treat all three detrimental results of atrial fibrillation and flutter is to actively interrupt all of the potential pathways for atrial reentry circuits.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive. Thus, despite its considerable clinical success, only a few maze procedures are done each year.

Maze-like procedures have also been developed utilizing catheters which can form lesions on the endocardium to effectively create a maze for electrical conduction in a predetermined path. Exemplary catheters are disclosed in commonly assigned U.S. Pat. No. 5,582,609. Typically, the lesions are formed by ablating tissue with one or more electrodes carried by the catheter. Electromagnetic radio frequency ("RF") energy applied by the electrodes heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue.

Catheters used to create lesions (the lesions being 3 to 15 cm in length) typically include a relatively long and relatively flexible body portion that has a plurality electrodes supported or near its distal end. The portion of the catheter body portion that is inserted into the patient is typically from 23 to 55 inches in length and there may be another 8 to 15 inches, including a handle, outside the patient. The proximal end of the catheter body is connected to the handle which includes steering controls. The length and flexibility of the catheter body allow the catheter to be inserted into a main vein or artery (typically the femoral artery), directed into the interior of the heart, and then manipulated such that the electrode contacts the tissue that is to be ablated. Fluoroscopic imaging is used to provide the physician with a visual indication of the location of the catheter.

Although catheter-based soft tissue coagulation has proven to be a significant advance in the medical arts generally and in the treatment of cardiac conditions in particular, it is not appropriate in every situation. Physicians may, for example, desire to perform a maze procedure as a supplemental procedure during an open heart surgical procedure such as a mitral valve replacement. Physicians may also desire to form lesions on the epicardial surface. Surgical probes which include a relatively short shaft that supports a plurality of electrodes have been introduced in recent years to facilitate the formation of lesions in these situations. Exemplary surgical probes are disclosed in commonly assigned U.S. Pat. No. 6,142,994, which is entitled "Surgical Method And Apparatus For Introducing Diagnostic And Therapeutic Elements Within The Body," which is incorporated here by reference.

Soft tissue coagulation that is performed using electrodes to transmit energy to tissue, whether catheter-based or surgical probe-based, may be performed in both bi-polar and uni-polar modes. Both modes require one or more indifferent return electrodes. In the uni-polar mode, energy emitted by the electrodes supported on the catheter or surgical probe is returned through one or more indifferent patch electrodes that are externally attached to the skin of the patient. Bi-polar devices, on the other hand, typically include a number of bi-polar electrode pairs. Both electrodes in each pair are supported by the catheter or surgical probe and energy emitted by one electrode in a particular pair is returned by way of the other electrode in that pair.

The uni-polar mode has proven to be superior to the bi-polar mode because the uni-polar mode allows for individual electrode control, while the bi-polar mode only allows electrode pairs to be controlled. Nevertheless, the inventor herein has determined that conventional uni-polar soft tissue coagulation techniques can be problematic because some patients have delicate skin and/or skin infections that preclude the attachment of an indifferent patch electrode to their skin. Poor indifferent electrode/skin contact can also be a problem, as can local burning. The inventor herein has also determined that it would be desirable to improve the likelihood that soft tissue coagulation procedures will result in transmural lesions, which is not always the case when conventional techniques are employed.

SUMMARY OF THE INVENTIONS

Accordingly, the general object of the present inventions is to provide methods and apparatus that avoid, for practical purposes, the aforementioned problems. In particular, one object of the present inventions is to provide methods and apparatus that can be used to create lesions in a more efficient manner than conventional apparatus. Another object of the present inventions is to provide methods and apparatus that facilitates uni-polar soft tissue coagulation without the problems associated with placing external patch electrodes on the patient's skin. Still another object of the present inventions is to provide methods and apparatus that are more likely to produce transmural lesions than conventional methods and apparatus.

In order to accomplish some of these and other objectives, an internal indifferent electrode device in accordance with a present invention includes a flexible shaft, an energy transmission device adapted to be inserted into the body supported on the shaft, and a connector adapted to mate with the power return connector of a power supply apparatus. There are a number of advantages associated with such a device. For example, the present internal indifferent electrode device may be placed within the patient and, therefore, allows physicians to perform uni-polar lesion formation procedures in such a manner that the issues associated with delicate skin and/or skin infections are eliminated.

In order to accomplish some of these and other objectives, a method in accordance with the present invention includes the steps of positioning an internal indifferent electrode device within the body on one side of a tissue structure wall, positioning an electrophysiological device within the body on the other side of the tissue structure wall, and transmitting energy from the electrophysiological device to the internal indifferent electrode device.

There are a number of advantages associated with such a method. For example, in one exemplary implementation, the internal indifferent electrode device will be placed in the blood pool within the left atrium and the electrophysiological device will be placed on the epicardial surface. Such an arrangement improves the lesion formation process and increases the likelihood of the formation of transmural lesions, as compared to epicardial processes where an external patch electrode is placed on the patient's skin, because the resistivity of blood is lower than that of other body tissue. The lowest resistivity path from the electrophysiological device to the indifferent electrode is, therefore, across the atrial wall and through the blood pool in the atrium. The present method also eliminates the indifferent electrode/skin contact problems associated with conventional methods. The flowing blood within the atrium will also cool the indifferent electrode, thereby reducing the likelihood of local tissue burning that is sometimes associated with external patch electrodes.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view showing an internal indifferent electrode device in accordance with a preferred embodiment of a present invention.

FIG. 2 section view taken along line 2-2 in FIG. 1.

FIG. 3 is a perspective view of one of the connectors in the internal indifferent electrode device illustrated in FIG. 1.

FIG. 5 is a plan view of an electrophysiological procedure kit including a surgical probe and an internal indifferent electrode device in accordance with a preferred embodiment of a present invention.

FIG. 6 is a plan view of the surgical probe illustrated in FIG. 5.

FIG. 7 is a partial section view of the distal portion of the surgical probe illustrated in FIGS. 5 and 6.

FIG. 8 is a section view taken along line 8-8 in FIG. 6.

FIG. 9 is a section view taken along line 9-9 in FIG. 7.

FIG. 10 is a section view of an alternative probe distal section.

DETAILED DESCRIPTION OF THE PREFERRED EMBODIMENTS

Figure 4:
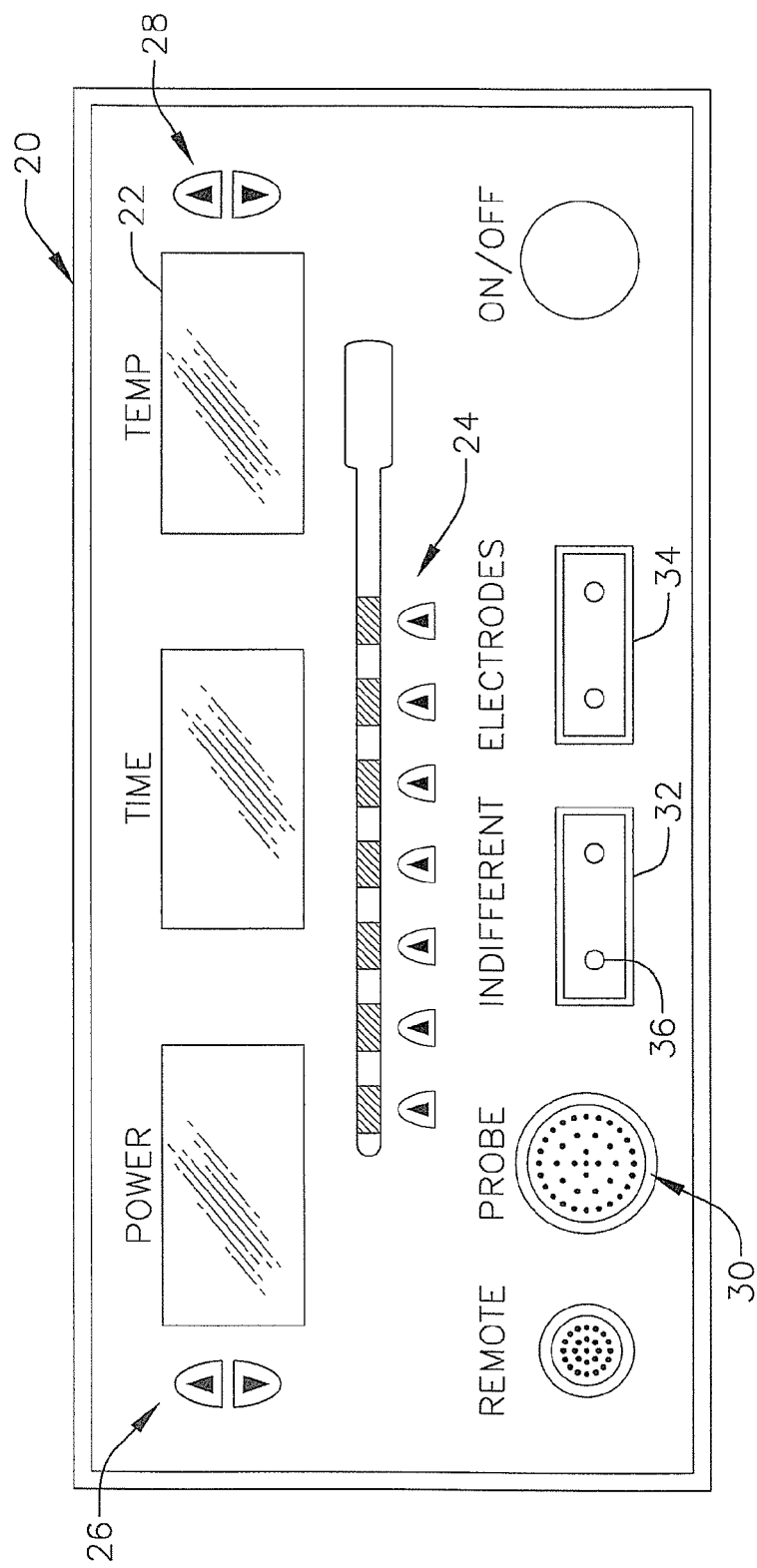
FIG. 4 is a front elevation view of an electrosurgical unit in accordance with a preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Internal Indifferent Electrode Device
   II. Electrophysiological Procedure Kit
   III. Electrodes, Temperature Sensing And Power Control
   IV. Methods The section titles and overall organization of the present detailed description are for the purpose of convenience only and are not intended to limit the present inventions.

This specification discloses a number of structures, mainly in the context of cardiac ablation, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Internal Indifferent Electrode Device

As shown by way of example in FIGS. 1-3, an internal indifferent electrode device 10 in accordance with a preferred embodiment of a present invention includes a shaft 12 that supports a plurality of electrodes 14. The electrodes 14 form part of a return path for tissue coagulation energy that is transmitted by another device in the manner discussed in greater detail below in Section IV below. Additional information concerning the type, size, structure and spacing of the electrodes 14, as well as other electrodes that may be employed in internal indifferent electrode devices, is provided in Section III below.

The shaft 12 should be between about 18 inches and about 24 inches in length, with an outer diameter between about 2 mm and about 4 mm. The exemplary embodiment, which is intended for use in cardiovascular applications, is about 18 inches in length with an outer diameter of about 3 mm. The shaft 12 should also be very flexible. Flexible biocompatible thermoplastic tubing such as unbraided Pebax® material, polyethylene, or polyurethane tubing may be used to form the shaft 12. The proximal end of the shaft 12 is connected to a base 16 by a cable 18. The base 16 is preferably formed from molded plastic. The cable 18, which is preferably formed from polyurethane tubing because this material is flexible and durable, will typically be about 10 feet long. An end cap (not shown) is secured within the distal end of the shaft 12.

The exemplary internal indifferent electrode device 10 is adapted to be used in conjunction with an automatic personality module (APM), such as the Model 882 sold by EP Technologies Inc. of San Jose, Calif., or an electrosurgical unit (ESU) such as the Model 4810 which is also sold by EP Technologies, Inc. and is generally represented by reference numeral 20 in FIG. 4. The exemplary ESU 20, which is used to supply and control power to a surgical probe or other electrophysiological device, includes a plurality of displays 22, as well as buttons 24, 26 and 28 that are respectively used to control which of the electrodes on the electrophysiological device receive power, the level of power supplied to the electrodes, and the temperature at the electrodes.

Power is supplied to the surgical probe or other electrophysiological device by way of a power output connector 30. Lesion creation procedures sometimes require that up to 2 amperes be returned to the ESU 20 and, to that end, two indifferent patch electrodes that can handle up to 1 ampere apiece are attached to the patient's skin and individually connected to the APM or ESU in conventional procedures. The indifferent patch electrodes are connected to a pair of power return connectors 32 and 34 on the ESU 20. a2

The exemplary internal indifferent electrode device 10 illustrated in FIGS. 1-3 is provided with eight spaced electrodes 14 that together act like a large single indifferent return electrode, thereby obviating the need for the conventional external patch electrodes described above. Each of the electrodes is connected to a respective wire 35 that runs through the shaft 12 and the cable 18 into the base 16. There, the wires are separated. Four of the wires 35 are connected to a connector 38 and the other four wires are connected to a connector 40. The power return connectors 32 and 34 in the exemplary ESU 20 illustrated in FIG. 4 each have a rectangular profile and recessed male pins 36, while the power output connector 30 has a circular profile. In order to mate with the rectangular power return connectors 32 and 34, the connectors 38 and 40 on the exemplary internal indifferent electrode device include a mating portion 42 with a rectangular profile and longitudinally extending female pin-connects 44. The profile need not be perfectly rectangular so long as the profile substantially corresponds to that of the power return connectors 32 and 34. For example, the middle of the top and bottom surfaces of mating portion 42 may include longitudinally extending grooves for mechanical keying with the corresponding connector.

Internal indifferent electrode devices in accordance with the present invention are not required to be configured in the manner described above. Instead, their configuration will depend upon the overall systems with which they are used and the requirements thereof. If, for example, an APM or ESU only included a single power return connector, then all of the wires 20 from the electrodes 14 would be connected to a single connector on the internal indifferent electrode device. Additionally, the shape and style of the power return connectors 32 and 34 and the corresponding mating portions 42 on the connectors 38 and 40 need not be rectangular. However, in preferred embodiments, both should have the same general shape and this shape should be different than the shape of the power output connector 30, which need not be circular, to prevent users from attempting to plug an indifferent electrode device into a power output connector and/or an electrophysiological device into a power return connector. Alternatively, the power output power return connectors could have the same general shape and noticeably different sizes to prevent confusion. Color coding may also be used.

A two-part base member including a re-usable proximal portion that supports the connectors 38 and 40, a disposable distal portion that supports the cable 18 and shaft 12, and a pair of mating PC cards that connect the two portions may also be used.

II. Electrophysiological Procedure Kit

As illustrated for example in FIG. 5, the internal indifferent electrode device 10 may form one portion of an electrophysiological procedure kit 46 that also includes a surgical probe 48 or some other device that is capable of transmitting energy through tissue to the internal indifferent electrode. Two examples of suitable surgical probes are the Cobra® surgical probe and the ThermaLine™ surgical probe, both manufactured by EP Technologies, Inc. in San Jose, Calif. Additional examples of surgical probes that may form a portion of the electrophysiological procedure kit 46 are provided in U.S. Pat. No. 6,142,994. The other tools and devices required for a particular procedure may be provided within the kit itself or simply provided separately.

The internal indifferent electrode device 10 and surgical probe 48 are housed in a sterile package 50 that has a flat rigid bottom portion 52 and a top transparent top cover 54 that provides recesses for the internal indifferent electrode device, surgical probe and any other included tools, thereby providing a ready to use surgical kit. The bottom portion 52 may be formed from Tyvek® spun bonded plastic fibers, or other suitable materials, which allow the contents of the package to be sterilized after the tools are sealed within the package.

Turning to FIGS. 6-10, the exemplary surgical probe 48 includes a relatively short shaft 50, a handle 52 and a distal section 54. The shaft 50 preferably consists of a hypotube 56, which is either rigid or relatively stiff, and an outer polymer tubing 58 over the hypotube. The shaft 50 in the illustrated embodiment may be from 4 inches to 18 inches in length, and is preferably 6 to 8 inches, while the distal section 54 may be from 1 inch to 10 inches in length, and is preferably 2 to 3 inches. The handle 52 preferably consists of two molded handle halves and is provided with strain relief element 60. A plurality of electrodes 62 or other energy transmission devices are provided on the distal section 54. There are seven electrodes 62 in the illustrated embodiment. Additional details concerning the electrodes 62 are provided in Section III below. A tissue cooling apparatus 64 is positioned over the electrodes 62 in the exemplary embodiment to cool tissue during lesion formation procedures.

The distal section 54 is preferably either entirely malleable, entirely somewhat flexible, or includes a malleable proximal portion and a somewhat flexible distal portion. A flexible version of the distal section 54 preferably includes a flexible spring member 66 that is secured to the hypotube 56 and enclosed in a flexible body 68 formed from Pebaxe material, polyurethane, or other suitable materials. [FIG. 9.] The distal end of the spring member 66 is secured to a tip member 70. An insulating sleeve 72 is placed over the spring member 66. The spring member 66 may be replaced by a malleable mandrel 74 that is secured to the hypotube 56 and tip member 70, as illustrated for example in FIG. 10. An insulating sleeve 76 is placed over the malleable mandrel 74. Another alternative arrangement is to have a distal section 54 that has a malleable proximal portion and a flexible distal portion composed of a short malleable mandrel and a short spring member that are secured to one another with a crimp tube. The short malleable mandrel would also be secured to the hypotube 56, while the short spring member would be secured to the tip member 70.

As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible elements are preferably formed from stainless steel, while malleable elements may be formed from annealed stainless steel or beryllium copper. With respect to the spring member, Nitinol as well as 17-7 and carpenter's steel are preferred. Additional information concerning the formation of, and materials for, the relatively short shaft 38 and the distal section 54 is provided in U.S. Pat. No. 6,142,994.

The exemplary tissue cooling apparatus 64 illustrated in FIGS. 6 and 7 employs conductive fluid to cool tissue during coagulation procedures. More specifically, heat from the tissue being coagulated is transferred to ionic fluid to cool the tissue while energy is transferred from the electrodes or other energy transmission device(s) to the tissue through the fluid by way of ionic transport. The conductive fluid is pumped through the tissue cooling apparatus 64, and preferably continuously, to cool tissue and facilitate the formation of lesions that are wider and deeper than those that could be realized with an otherwise identical device which lacks the cooling apparatus.

The exemplary tissue cooling apparatus 64 includes a microporous outer casing 78 mounted on the probe distal section 54 over the electrodes 62. The proximal and distal ends of the outer casing 78 are secured with anchoring devices 80 and 82 that are preferably formed from heat shrink tubing. A fluid transmission space 84 between the inner surface of the outer casing 78 and the outer surface of the distal section 54 and electrodes 62 extends uninterrupted from a fluid supply line 86 to a fluid drainage tube 88. [Note arrows F.] The ends of the supply line 86 and drainage tube 88 that terminate within the outer casing 78 are secured with anchoring devices 80 and 82. The fluid supply line 86 is also secured to the exterior of shaft 50 with an anchoring device 90.

The microporous outer casing 78 should be no larger than 3 times the diameter of the electrodes 62 and will preferably be 1.2 to 2 times the electrode diameter. This translates to a fluid transmission space 84 that is typically about 0.005 to 0.020 inch, measured inner surface to outer surface, but can be as large as 0.1 inch. Of course, other sizes may be used if they are required by a particular application.

The ionic fluid, which is supplied under pressure from a fluid source (not shown) to fluid supply line 86, heats up as it passes through the transmission space 84. The drainage tube 88 directs heated ionic fluid into a receptacle outside the patient. Removal of the heated ionic fluid is important because it will be hot enough (typically about 60° C. when it reaches the distal end of the probe) to burn the patient if allowed to drip into the thorax.

The electrically conductive ionic fluid preferably possesses a low resistivity to decrease ohmic loses, and thus ohmic heating effects, within the microporous outer casing 78. The composition of the electrically conductive fluid can vary. In the illustrated embodiment, the fluid is a hypertonic saline solution, having a sodium chloride concentration at or near saturation, which is about 5% to about 25% weight by volume. Hypertonic saline solution has a relatively low resistivity of only about 5 ohm-cm, as compared to blood resistivity of about 150 ohm-cm and myocardial tissue resistivity of about 500 ohm-cm. Alternatively, the ionic fluid can be a hypertonic potassium chloride solution.

With respect to temperature and flow rate, a suitable inlet temperature for epicardial applications (the temperature will, of course, rise as heat is transferred to the fluid) is about 0 to 25° C. with a constant flow rate of about 2 to 20 ml/min. The flow rate required for endocardial applications where blood is present would be about three-fold higher (i.e. 6 to 60 ml/min.). Should applications so require, a flow rate of up to 100 ml/min. may be employed. In a closed system where the fluid is stored in a flexible bag, such as the Viaflex® bag manufactured by Baxter Corporation, and heated fluid is returned to the bag, it has been found that a volume of fluid between about 200 and 500 ml within the bag will remain at room temperature (about 22° C.) when the flow rate is between about 2 ml/min. and 20 ml/min. Alternatively, in an open system, the flexible bag should include enough fluid to complete the procedure. 160 ml would, for example, be required for a 20 minute procedure where the flow rate was 8 ml/min.

The fluid pressure within the microporous outer casing 78 should be about 30 mm Hg in order to provide a structure that will resiliently conform to the tissue surface in response to a relatively small force normal to the tissue. Pressures above about 100 mm Hg will cause the outer casing 78 to become too stiff to properly conform to the tissue surface. For that reason, the flow resistance to and from the outer casing 78 should be relatively low.

The pores in the microporous outer casing 78 allow the transport of ions contained in the fluid through the casing and into contact with tissue. Thus, when the electrodes 62 transmit RF energy into the ionic fluid, the ionic fluid establishes an electrically conductive path through the outer casing 78 to the tissue being coagulated. Regenerated cellulose membrane materials, typically used for blood oxygenation, dialysis, or ultrafiltration, are a suitable microporous material for the outer casing 78. The thickness of the material should be about 0.002 to 0.005 inch. Although regenerated cellulose is electrically non-conductive, the relatively small pores of this material allow effective ionic transport in response to the applied RF field. At the same time, the relatively small pores prevent transfer of macromolecules through the material, so that pressure driven liquid perfusion is less likely to accompany the ionic transport, unless relatively high pressure conditions develop within the outer casing 78.

Hydro-Fluro™ material, which is disclosed in U.S. application Ser. No. 09/573,071, filed May 16, 2000, and incorporated herein by reference, is another material that may be used. Materials such as nylons (with a softening temperature above 100° C.), PTFE, PEI and PEEK that have micropores created through the use of lasers, electrostatic discharge, ion beam bombardment or other processes may also be used. Such materials would preferably include a hydrophilic coating. Microporous materials may also be fabricated by weaving a material (such as nylon, polyester, polyethylene, polypropylene, fluorocarbon, fine diameter stainless steel, or other fiber) into a mesh having the desired pore size and porosity. These materials permit effective passage of ions in response to the applied RF field. However, as many of these materials possess larger pore diameters, pressure driven liquid perfusion, and the attendant transport of macromolecules through the pores, are also more likely to occur. Considerations of overall porosity (discussed below) and perfusion rates must be taken more into account as pore size increases.

The electrical resistivity of the outer casing 78 will have a significant influence on lesion geometry and controllability. Low-resistivity (below about 500 ohm-cm) requires more RF power and results in deeper lesions, while high-resistivity (at or above about 500 ohm-cm) generates more uniform heating and improves controllability. Because of the additional heat generated by the increased body resistivity, less RF power is required to reach similar tissue temperatures after the same interval of time. Consequently, lesions generated with high-resistivity structures usually have smaller depth. The electrical resistivity of the outer casing can be controlled by specifying the pore size of the material, the porosity of the material, and the water adsorption characteristics (hydrophilic versus hydrophobic) of the material. A detailed discussion of these characteristics is found in U.S. Pat. No. 5,961,513, which is entitled "Tissue heating and Ablation Systems and Methods Using Porous Electrode Structures" and is incorporated herein by reference. A suitable electrical resistivity for epicardial and endocardial lesion formation is about 1 to 3000 ohm-cm measured wet.

Generally speaking, low or essentially no liquid perfusion through the microporous outer casing 78 is preferred. When undisturbed by attendant liquid perfusion, ionic transport creates a continuous virtual electrode at the electrode body-tissue interface. The virtual electrode efficiently transfers RF energy without need for an electrically conductive metal surface.

Pore diameters smaller than about 0.1 μm retain macromolecules, but allow ionic transfer through the pores in response to the applied RF field. With smaller pore diameters, pressure driven liquid perfusion through the pores is less likely to accompany the ionic transport, unless relatively high pressure conditions develop within the outer casing 78. Larger pore diameters (up to 8 μm) can also be used to permit ionic current flow across the membrane in response to the applied RF field. With larger pore diameters, pressure driven fluid transport across the membrane is much higher and macromolecules (such as protein) and even small blood cells (such as platelets) could cross the membrane and contaminate the inside of the probe. Red blood cells would normally not cross the membrane barrier, even if fluid perfusion across the membrane stops. On balance, a pore diameter of 1 to 5 μm is suitable for epicardial and endocardial lesion formation. Where a larger pore diameter is employed, thereby resulting in significant fluid transfer through the porous region, a saline solution having a sodium chloride concentration of about 0.9% weight by volume would be preferred.

With respect to porosity, which represents the volumetric percentage of the outer casing 78 that is composed of pores and not occupied by the casing material, the magnitude of the porosity affects electrical resistance. Low-porosity materials have high electrical resistivity, whereas high-porosity materials have low electrical resistivity. The porosity of the outer casing 78 should be at least 1% for epicardial and endocardial applications employing a 1 to 5 μm pore diameter.

Turning to water absorption characteristics, hydrophilic materials are generally preferable because they possess a greater capacity to provide ionic transfer of RF energy without significant liquid flow through the material.

Certain other considerations are applicable to those embodiments which are endocardial in nature and, therefore, operate within the blood pool. Most notably, there should be essentially no liquid perfusion. This limits salt or water overloading caused by transport of the hypertonic solution into the blood pool. This is especially true when the hypertonic solution includes potassium chloride. Additionally, the ionic transport rate should below about 10 mEq/min when the hypertonic solution includes potassium chloride.

Nonporous outer casings (not shown) that are both electrically and thermally conductive may be used in place of the porous outer casing 78. A nonporous outer casing may, for example, have the same configuration as the porous outer casing 78. As with the porous outer casing, the resistivity across the nonporous outer casing should be about 1 ohm-cm to about 3000 ohm-cm measured wet. The nonporous outer casing should also enable a transfer of 10 W of power with a 10° C. temperature gradient across the nonporous outer casing for each cm of length, as should the porous outer casing 78. For example, at least 80 W of thermal energy should transfer across a 4 cm length of outer casing if there exists a 20° C. temperature difference between the inner and outer casing surfaces. Suitable materials for the conductive nonporous outer casing include plastic materials (such as polyurethane) which are highly loaded with metallic additives or carbon fibers. Elastomers (such as silicone rubber) can also be loaded with conductive additives to achieve thermal and electrical conductivities in the ranges required for this application.

Other methods of cooling tissue may also be employed where appropriate. Suitable methods include Joule-Thompson cooling, Peltier diode cooling (cooling using semiconductor devices that generate heat on one side while heat is removed on the other) and, in the context of wettable fluid retention elements, active vaporization.

Figure 11:
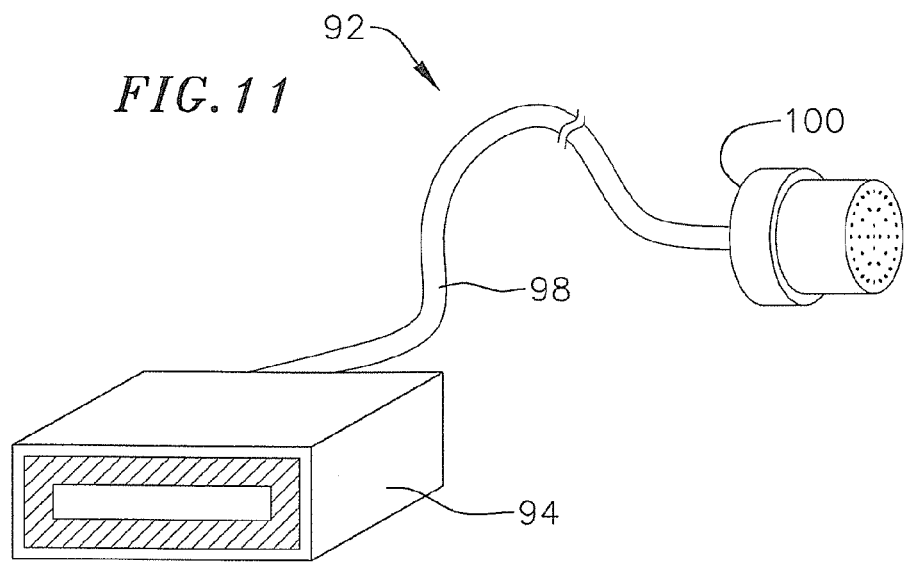
FIG. 11 is a perspective view of a surgical probe connection device in accordance with a preferred embodiment of a present invention.

As illustrated for example in FIG. 11, the exemplary surgical probe 48 may be provided with a connection device 92 that connects the surgical probe to the ESU 20. The connection device 92 includes a connector 94 that may be inserted into an opening 96 in surgical probe handle 52 (FIG. 6), a cable 98, and a connector 100 that has a shape and size corresponding to that of the power output connector 30 on the ESU 20 (FIG. 4).

Additional details concerning the surgical probe 48 and other similar devices is provided in U.S. patent application Ser. No. 09/761,981, which is entitled "Fluid Cooled Apparatus For Supporting Diagnostic And Therapeutic Elements In Contact With Tissue" and incorporated herein by reference.

III. Electrodes, Temperature Sensing And Power Control

The electrodes 14 and 62 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred design is disclosed in U.S. Pat. No. 5,797,905.

Alternatively, the electrodes 14 and 62 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed. Referring more specifically to the electrodes 62 on the surgical probe 48, given that the purpose of the electrodes 62 is to transfer energy into the ionic fluid, as opposed to directly into tissue, the electrodes 62 may even be replaced by a straight piece of bare wire.

The exemplary electrodes 14 on the internal indifferent electrode device 10 are preferably 12.5 mm long coil electrodes with 3 mm spacing. This arrangement will prevent any one of the electrodes 14 from functioning as a lesion forming device because the large overall surface area of the electrodes ensures that the current density is low enough to prevent significant heating. Nevertheless, the electrodes 14 may range from about 4 mm to about 100 mm in length and the exemplary plurality of spaced electrodes may be replaced by a relatively long single coil electrode or other energy transmission device.

The exemplary electrodes 62 are preferably coil electrodes that are about 4 mm to about 20 mm in length. In the preferred embodiments, the electrodes 62 are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

Referring to FIGS. 6-10, RF power (or other power) from an ESU 20 or other power supply and control device is supplied to the electrodes 62 by conducting wires 102. The conducting wires 102 are connected to a PC board 104, which is located within the handle 52 and adapted to mate with the connector 94. A plurality of temperature sensors 106, such as thermocouples or thermistors, may be located on, under, abutting the longitudinal end edges of, or in between, the electrodes 62. Alternatively, a sensor could simple be located at or near the location where the fluid exits the tissue cooling apparatus 64 in order to determine the temperature of the fluid at its hottest point. Signals from the temperature sensors are transmitted to the power supply and control device by way of wires 108 that are also connected to the PC board 104. A reference thermocouple may also be provided if desired. Suitable temperature sensors and power supply and control devices are disclosed in U.S. Pat. Nos. 5,456,682, 5,582,609 and 5,755,715.

The amount of power required to coagulate tissue ranges from 5 to 150 w and depends on parameters such as set temperature and the flow rate of the ionic fluid. For epicardial lesion formation using the cooling apparatus 64 illustrated FIGS. 6 and 7 with a 6 mm diameter, it has been found that an 80° C. electrode temperature can be maintained with a 8 ml/min. ionic fluid flow rate when 75 w of power is supplied to each electrode for about 60 seconds. It has been found that these parameters produce lesions, both epicardial and endocardial that are at least 20 mm wide and 18 mm deep.

High voltage gradients have also been used to create lesions by dielectrically breaking down cell membranes to kill tissue. Voltage gradients above 500V/cm created by short bursts of RF current are preferred. In the context of the present inventions, placing the exemplary internal indifferent electrode device 10 inside a heart chamber (such as the left atrium) and the surgical probe electrodes 62 on the epicardial surface would increase the voltage gradient across the heart wall as compared to situations where a conventional patch electrode is placed on the patient's skin. Such an arrangement also limits peripheral tissue damage. Additional information concerning the use of high voltage gradients to create lesions is provided in U.S. Pat. No. 6,107,699.

IV. Methods

Figure 12:
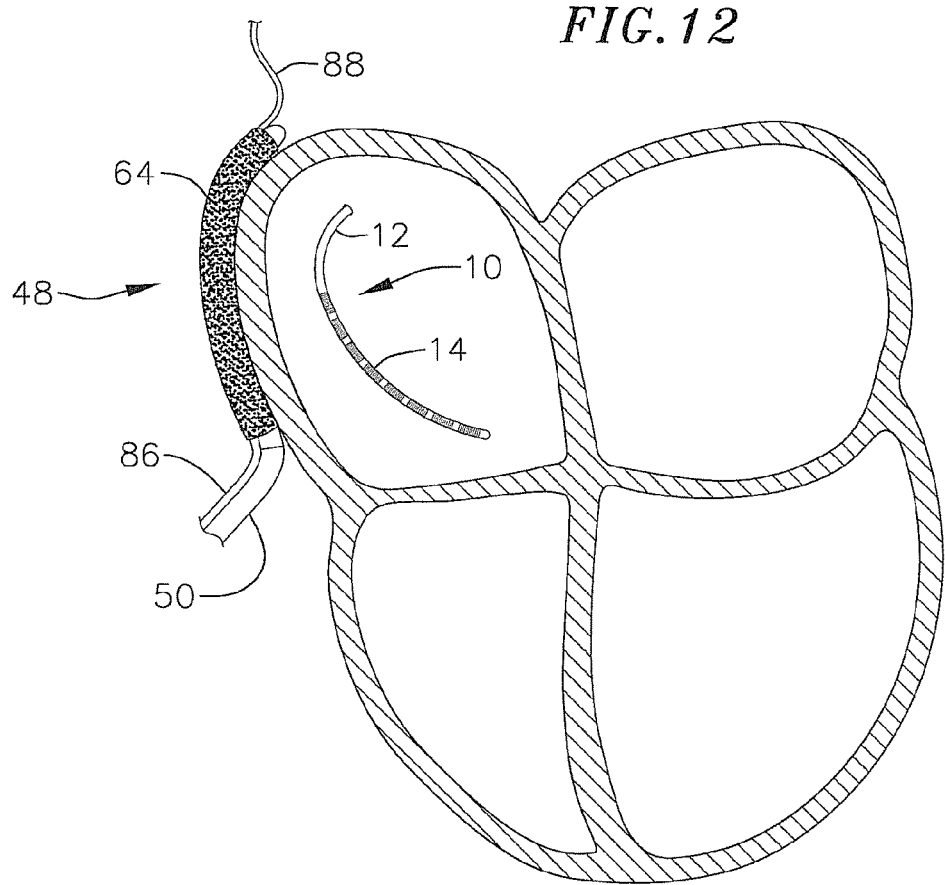
FIG. 12 is a section view of a human heart during a lesion formation procedure employing the surgical probe and internal indifferent electrode kit illustrated in FIG. 5.

The formation of epicardial lesions is one example of a procedure that may be performed in accordance with the present inventions. As illustrated for example in FIG. 12, an internal indifferent electrode device, such as the exemplary internal indifferent electrode device 10, may be placed within the blood pool in the left atrium during an epicardial lesion formation procedure in which an energy transmitting device, such as the energy transmitting portion of the surgical probe 48, is placed on the epicardial surface. The internal indifferent electrode device may, alternatively, be placed within other open spaces within the heart such as the superior vena cava, the inferior vena cava or the other chambers depending on the location of the energy transmitting device.

Access to the heart may be obtained via a thoracotomy, thoracostomy or median sternotomy. Ports may also be provided for cameras and other instruments. The internal indifferent electrode device 10 may be inserted into the atrium through an atrial appendage and a purse string technique may be used to secure it in place and prevent the flow of blood through the appendage. Alternatively, the internal indifferent electrode device 10 may be inserted into the atrium by way of the jugular vein using a Seldinger technique.

Tissue coagulating energy from the surgical probe electrodes 62 will be transmitted across the atrial wall and through the blood in the left atrium to the electrodes 14 on the internal indifferent electrode device 10 to form the transmural lesion in the atrial wall. Additional lesions may be formed by moving the energy transmitting portion of the surgical probe 48 to other places on the epicardial surface and transmitting energy through tissue to the internal indifferent electrode device 10. The internal indifferent electrode device 10 may also be moved as necessary.

There are a number of advantages associated with placing the an internal indifferent electrode device within the blood pool in the heart, as opposed to the patients skin. For example, the resistivity of blood is relatively low (about 150 ohm-cm)

as compared to other body tissues, while the internal indifferent electrode device adds less impedance than do external patch electrodes. Thus, the effectiveness of the lesion formation process will be improved because the lowest impedance path from the surgical probe electrodes 62 to the return electrodes 14 on the internal indifferent electrode device 10 is directly across the atrial wall and through the blood. The flowing blood will also cool the electrodes 14, thereby reducing the likelihood of local tissue burning that is sometimes associated with external patch electrodes. Additionally, poor tissue contact, which can create problems when external patch electrodes are employed, is not an issue when an internal indifferent electrode device is placed into the blood pool.

The present lesion formation methods in accordance with the present inventions may also be practiced with catheters. For example, instead of surgically inserting the exemplary internal indifferent electrode 10 into heart, a catheter including one or more indifferent electrodes may be percutaneously advanced into the left atrium or another region or chamber within the heart.

Once the indifferent electrode(s) on the catheter are in the blood pool, tissue coagulating energy may be delivered to the epicardial surface by, for example, the electrodes on the surgical probe 48 to form a transmural lesion in the manner described above. Alternatively, instead of employing a surgical probe, a catheter carrying one or more energy emitting electrodes my be percutaneously directed to a different region or chamber than the catheter that is carrying the indifferent electrodes. The energy emitting electrodes on the catheter may then be used to transmit energy across an internal wall within the heart to the indifferent electrodes on the other catheter to create a transmural lesion.

Regardless of the type of device supporting the indifferent electrodes in the above-described lesion formation methods, the indifferent electrodes will normally be slightly spaced from the endocardial surface. Nevertheless, should it be desired that the indifferent electrodes also function as coagulation electrodes to further increase the likelihood of a transmural lesion, they may be positioned against the endocardial surface in close proximity to the electrodes on the epicardial surface (or other side of an internal wall) that are transmitting the energy.

Although the present inventions have been described in terms of the preferred embodiments above, numerous modifications and/or additions to the above-described preferred embodiments would be readily apparent to one skilled in the art. For example, the scope of the inventions includes any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. An internal indifferent electrode for use with a power supply apparatus including a power output connector and first and second power return connectors, the internal indifferent electrode device comprising:
    a flexible shaft defining a distal end, a distal portion, a proximal end and a proximal portion;
    first and second indifferent electrode connectors, each with at least one connector element, operably connected to the flexible shaft and respectively configured to mate with the first and second power return connectors of the power supply apparatus; and
    a first plurality of spaced energy transmission devices connected to the first indifferent electrode connector and a second plurality of spaced energy transmission devices connected to the second indifferent electrode connector.

2. An internal indifferent electrode device as claimed in claim 1, wherein the plurality of spaced energy transmission devices comprises a plurality of spaced electrodes.

3. An internal indifferent electrode device as claimed in claim 1, wherein the plurality of spaced energy transmission devices comprises a plurality of spaced flexible electrodes.

4. An internal indifferent electrode device as claimed in claim 1, wherein the at least one connector element comprises a pin-type connector element.

5. An internal indifferent electrode device as claimed in claim 1, wherein the at least one connector element comprises a plurality of pin-type connector element.

* * * * *

UNITED STATES PATENT AND TRADEMARK OFFICE
CERTIFICATE OF CORRECTION

PATENT NO. : 8,758,335 B2
APPLICATION NO. : 11/864567
DATED : June 24, 2014
INVENTOR(S) : Swanson It is certified that error appears in the above-identified patent and that said Letters Patent is hereby corrected as shown below:

In the Specification

Column 8
Line 38: after "25° C", delete "."
Line 47: after "(about 22° C", delete "."

Column 9
Line 15: after "above 100° C", delete "."

Signed and Sealed this
Ninth Day of September, 2014

Michelle K. Lee
*Deputy Director of the United States Patent and Trademark Office*